(12) United States Patent
Lee et al.

(10) Patent No.: US 6,177,610 B1
(45) Date of Patent: Jan. 23, 2001

(54) MAJOR BASIC PROTEIN DEFICIENT ANIMALS

(75) Inventors: James J. Lee; Nancy A. Lee, both of Scotsdale; Karen L. Denzler, Phoenix; Steven C. Farmer, Mesa, all of AZ (US)

(73) Assignee: Mayo Foundation for Medical Education and Research, Rochester, MN (US)

( * ) Notice: Under 35 U.S.C. 154(b), the term of this patent shall be extended for 0 days.

(21) Appl. No.: 09/210,017

(22) Filed: Dec. 11, 1998

(51) Int. Cl.[7] .......................... C12N 15/11; C12N 19/63; C12N 15/85; A01K 67/00
(52) U.S. Cl. ..................... 800/18; 800/8; 800/9; 800/13; 800/14; 800/18; 435/320.1; 435/325; 536/23.1; 536/23.5
(58) Field of Search .................. 536/23.1, 23.5; 435/320.1, 325; 800/3, 8, 14, 18

(56) References Cited

PUBLICATIONS

Mullins et al., J. Clin. Invest., vol. 98, pp. S37–S41, 1996.*
Moreadith et al., J. Mol. Med., vol. 75, pp. 208–216, 1997.*
Aszodi et al., J. Molecular Med., vol. 76, pp. 238–252, 1998.*
Wall, Theriogenology, vol. 45, pp. 57–68, 1996.*
Daniels et al., "A genome–wide search for quantitative trait loci underlying asthma", Nature, 1996, 383:247–250.
McBride et al., "Inflammatory Effects of Ozone in the Upper Airways of Subjects with Asthma", Am. J. Resp. Crit. Care Med., 1994, 149(5):1192–1197.
O'Byrne et al., "Allergen–induced airway hyperresponsiveness", J. Allergy. Clin. Immunol., 1988, 81(1):119–127.
Gleich et al., "Bronchial Hyperreactivity and Eosinophil Granule Proteins", Agents Actions Suppl., 1993, 43:223–230.
Rochester et al., "Eosinophil–Fibroblast Interactions — Granule Major Basic Protein Interacts with IL–1 and Transforming Growth Factor–$\beta$ in the Stimulation of Lung Fibroblast IL–6–Type Cytokine Production", J. Immunol., 1996, 156(11):4449–4456.
Patella et al., "Eosinophil Granule Proteins Activate Human Heart Mast Cells", J. Immunol., 1996, 157(3):1219–1225.
Abu–Ghazaleh et al., "Interaction of Eosinophil Granule Major Basic Protein with Synthetic Lipid Bilayers: A Mechanism for Toxicity", J. Membrane Biol., 1992, 128(2):153–164.
O'Donnell et al., "Activation of Basophil and Mast Cell Histamine Release by Eosinophil Granule Major Basic Protein", J. Exp. Med., 1983, 157(5):1981–1991.
Shastry, "Gene disruption in mice: Models of development and disease", Mol. Cell Biochem., 1998, 181(1–2):163–179.
Lee et al., "Interleukin–5 Expression in the Lung Epithelium of Transgenic Mice Leads to Pulmonary Changes Pathognomonic of Asthma", J. Exp. Med., 1997, 185(12):2143–2156.
Blyth et al., "Lung Inflammation and Epithelial Changes in a Murine Model of Atopic Asthma", Am. J. Respir. Cell Mol. Biol., 1996, 14(5):425–438.
Larson et al., "The Identification and Cloning of a Murine Major Basic Protein Gene Expressed in Eosinophils", J. Immunol., 1995, 155(6):3002–3012.
Hamelmann et al., "Noninvasive Measurement of Airway Responsiveness in Allergic Mice Using Barometric Plethysmography", Resp. Crit. Care med., 1997, 156(2):766–775.

* cited by examiner

Primary Examiner—John L. LeGuyader
Assistant Examiner—Michael C. Wilson
(74) Attorney, Agent, or Firm—Fish & Richardson, P.C., P.A.

(57) ABSTRACT

Major basic protein deficient non-human mammals that contain an inactivated major basic protein allele are described. A nucleic acid construct including an inactivated major basic protein gene is also described.

7 Claims, 6 Drawing Sheets

Wild-type (+/+)

MAJOR BASIC PROTEIN DEFICIENT ANIMALS

STATEMENT AS TO FEDERALLY SPONSORED RESEARCH

Funding for the work described herein was provided, in part, by the federal government, which may have certain rights in the invention.

TECHNICAL FIELD

The invention relates to major basic protein (MBP) deficient animals.

BACKGROUND OF THE INVENTION

The management of asthma has changed significantly over the past decade, reflecting the recognition of a coincident chronic pulmonary inflammation. Asthma appears to be pluricausal in origin, involving several genes and exacerbating factors, such as air pollution, allergies, cold sensitivity, viral infection, and tobacco/chemical exposure. See, for example, Daniels, S. E. et al., *Nature*, 383(6597):247–250, 1996; McBride, D. E. et al., *Am. J. Resp. Crit. Care Med.*, 149(5):1192–1197, 1988; and O'Byrne, P. M., *J. Aller. Clin. Immunol.*, 81(1):119–127, 1988. The wide variability among patients, both in terms of etiology and presentation of symptoms, is anchored by three common characteristic features: reversible variable airflow limitations, specific airway histopathologies, and airway hyperresponsiveness (AHR, i.e., the development of bronchoconstriction in response to nonspecific stimuli). Additional indicators of asthma include mucus overproduction, increased expression of IL-4 and IL-5, increased serum IgE levels, and often (70–90% of reported cases) the increased presence of eosinophils in the airway mucosa and lumen. The pathophysiological manifestations of asthma correlate with this eosinophilic airway infiltration. Indeed, eosinophil influx has been associated with the development of lung dysfunction even in mild cases of asthma. The concurrent appearance of pulmonary pathologies and eosinophil recruitment to the lung suggests that a causative relationship exists.

Eosinophil effector functions are mediated by several concurrent mechanisms including the secretion of small molecule mediators of inflammation (e.g., PAF, leukotrienes, proinflammatory cytokines such as interleukins 4, 5, and 8), antigen presentation and the release of granule components (i.e., degranulation). These mechanisms contribute to several inflammatory pathways. For example, secretion of inflammatory signals by eosinophils results in vasodilation and tissue edema and the recruitment/activation of other effector cells. Moreover, the ability of eosinophils to act as antigen presentation cells suggests that their recruitment to the lung during allergic inflammation may result in presentation of aeroallergens to resident T cells and thus initiate and/or amplify pulmonary immune responses.

A growing literature exists indicating that the release of eosinophil secondary granule proteins (ESGPs) is a critical effector function. ESGPs effector functions include not only cytotoxic activities leading to airway damage and lung dysfunction (e.g., AHR), but also agonist activities on several other cell types. Gleich, G. J. and C. Adolphson, *Agents Actions Suppl.*, 43:223–230, 1993. For example, in vitro studies of lung fibroblasts have shown that ESGPs are capable of modulating gene expression from these cells. Rochester, C. L. et al., *J. Immunol.*, 156(11):4449–4456, 1996. Furthermore, ESGPs also modulate the activation state and genes expressed by other leukocyte effector cells including neutrophils and mast cells. Agonist activities also extend to autocrine effects on eosinophils leading to the expression of inflammatory mediators and eosinophil degranulation. Patella, V. et al., *J. Immunol.*, 157(3):1219–1225, 1996. These studies suggest that the interplay of ESGP effector functions have pleiotropic effects on the lung resulting in both tissue destruction and the modulation of inflammatory responses associated with allergic pulmonary inflammation. The four prominent murine secondary granule constituents include eosinophil peroxidase (EPO), major basic protein (MBP), and eosinophil associated ribonucleases (EAR-1 and EAR-2). EPO, MBP, eosinophil cationic protein (ECP), and eosinophil-derived neurotoxin (EDN) are the prominent secondary granule constituents in humans.

SUMMARY OF THE INVENTION

As described herein, MBP deficient animals fail to exhibit airway hyperresponsiveness. Thus, the release of MBP is linked to a lung disfunction in asthmatic patients. MBP deficient animals can be used in conjunction with wild-type animals to screen for anti-MBP therapies.

In one aspect, the invention features a DNA construct that includes an inactivated MBP gene, wherein the inactivation is due to disruption of a sequence in the gene such that expression of functional MBP is prevented. The inactivated MBP gene may lack exons 2, 3 and 4.

The invention also features a non-human mammal, and progeny thereof, that include an inactivated MBP gene, wherein the inactivation results in reduced levels of endogenous MBP in the non-human mammal. The non-human mammal can be heterozygous or homozygous for the inactivated MBP gene. In one embodiment, the non-human mammal lacks MBP. The non-human mammal can be, for example, a rodent, and in particular, a mouse. Non-human mammals of the invention do not exhibit airway hyperresponsiveness. The non-human mammal also can include a human MBP gene.

Non-human mammal eosinophil cells lacking MBP also are featured. The cells can be murine eosinophil cells. Murine eosinophil cells can be isolated from a mouse homozygous for an inactivated MBP gene, wherein the inactivation results in a mouse lacking MBP.

The invention also relates to a method for identifying inhibitors of MBP effector function that includes comparing airway hyperresponsiveness of a first non-human mammal in the presence of a compound with a second non-human mammal in the absence of the compound. The first and second non-human mammals each include a human MBP gene and an inactivated endogenous MBP gene, such that the first and second non-human mammals each have detectable levels of human MBP and reduced levels of endogenous MBP. Compounds are identified as inhibitors of MBP effector function if airway hyperresponsiveness is reduced in the first non-human mammal. The first and second non-human mammals can be rodents, and in particular, can be mice.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

MBP is a small cationic protein that forms the characteristic crystalline core of secondary granules. Although enzymatic functions have not been attributed to MBP, it exhibits both cytotoxic and cell agonist activities. Abu-Ghazaleh, R. I. et al., *J. Membr. Biol.*, 128(2):153–164, 1992; and O'Donnell, M. C. et al., *J. Exp. Med.,* 157(6):1981–1991, 1983. Deposition of MBP is common in the lungs of asthmatics, accompanying airway epithelial damage and the appearance of airway hyperresponsiveness (AHR). As described herein, AHR in animal models of respiratory inflammation is contingent upon the presence of MBP. Thus, AHR, the hallmark feature of asthma, appears to result from the release of MBP from eosinophils in response to allergic inflammation.

Production of MBP Deficient Animals

The invention features non-human mammals including an inactivated MBP gene, and progeny and cells of such animals. Inactivation of the MBP gene results in non-human mammals with reduced levels of MBP, when compared with a corresponding wild-type animal. MBP deficient animals also are referred to as "knockout animals". Animals can be heterozygous and have one inactivated MBP allele, or can be homozygous and have two inactivated alleles. Non-human mammals that are homozygous for an inactivated MBP allele lack MBP. Non-human mammals include, for example, rodents such as rats, guinea pigs, and mice, and farm animals such as pigs, sheep, goats, horses and cattle. MBP deficient mice are particularly useful.

Constructs for inactivating the MBP gene by homologous recombination can be made by interrupting the MBP gene within an appropriate coding exon. See, Shastry, B. S., *Mol. Cell Biochem.,* 181(1–2):163–179, 1998, for a review of gene targeting technology. For example, analysis of the nucleic acid sequence encoding murine MBP (mMBP) indicates that exons 2–4 are preferred locations for disruption of this gene by homologous recombination. However, identification of these exons as preferred sites should not be construed as limiting the scope of the present invention, as interruptions in exons 1, 5 and 6 also can be useful. Moreover, regulatory elements associated with the coding sequence also can present useful targets for inactivation. The coding sequence of mMBP has GenBank Accession No. L46768.

A nucleic acid sequence encoding a selectable marker is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3' phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex. Constructs utilizing both positive and negative drug selection also can be used. For example, a construct can contain the aminoglycoside phosphotransferase gene and the TK gene. In this system, cells are selected that are resistant to G418 and sensitive to gancyclovir. Any selectable marker suitable for inclusion in a knockout vector is within the scope of the present invention.

To create animals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent". Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking a functional MBP gene. That is, cultured ES cells can be transformed with a knockout construct and cells selected in which the MBP gene is inactivated.

Nucleic acid constructs can be introduced into ES cells, for example, by electroporation or other standard technique.

Selected cells can be screened for gene targeting events. For example, the polymerase chain reaction (PCR) can be used to confirm the presence of the transgene. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA (reverse-transcriptase PCR, RT-PCR), including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplified. See, for example, Lewis, R. *Genetic Engineering News*, 12(9):1, 1992; Guatelli et al., *Proc. Natl. Acad. Sci. USA*, 87:1874–1878, 1990; and Weiss, R., *Science*, 254:1292, 1991.

The ES cells further can be characterized to determine the number of targeting events. For example, genomic DNA can be harvested from ES cells and used for Southern analysis. See, for example, Section 9.37–9.52 of Sambrook et al., "Molecular Cloning, A Laboratory Manual, second edition, Cold Spring Harbor Press, Plainview; N.Y., 1989.

To generate a knockout animal, ES cells having at least one inactivated MBP allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated MBP allele. If the original ES cell was heterozygous for the inactivated MBP allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are "totipotent", i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the MBP gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated MBP gene, and then fused with enucleated oocytes. After activation of the oocytes, the eggs are cultured to the blastocyst stage, and implanted into a recipient. See, Cibelli, J. B. et al., *Science*, 280:1256–1258, 1998. Adult somatic cells, including, for example, cumulus cells and mammary cells, can be used to produce animals such as mice and sheep, respectively. See, for example, Wakayama, T. et al., *Nature*, 394(6691):369–374, 1998; and Wilmut, I. et al., *Nature*, 385(6619):810–813, 1997. Nuclei can be removed from genetically modified adult somatic cells, and transplanted into enucleated oocytes. After activation, the eggs can be cultured to the 2–8 cell stage, or to the blastocyst stage, and implanted into a suitable recipient. Wakayama, T. et al., 1998, supra.

Phenotype of MBP Deficient Animals

Animals having either one (heterozygous) or two (homozygous) inactivated MBP genes are characterized to confirm the expected alterations in gene expression and to determine the phenotypic effect. For example, MBP mRNA should be absent from homozygous knockout animals, and may be present in reduced levels in heterozygous animals. This can be confirmed, for example, with RT-PCR using appropriate MBP-specific primers. In addition, various tests can be performed to evaluate expression of the MBP epitope in animals. Anti-MBP antibodies can be used in various assays or immunohistological formats to demonstrate the loss of MBP. An anti-MBP antibody is described, for example, in Lee, J. J. et al., *J. Exp. Med.*, 185:2143–2156, 1997. Alternatively, electron microscopy can be used to examine eosinophils for electron dense regions present in the eosinophil granules. As described herein, eosinophils from homozygous animals lack electron dense regions in the granules, whereas eosinophil granules with electron dense regions are present in both heterozygous and wild-type animals. This suggests that core formation is dependent on the presence of MBP.

Non-human mammals of the invention that are deficient in MBP do not exhibit AHR. In typical animal models of pulmonary inflammation, animals are sensitized with a specific antigen such as ovalbumin (OVA) followed by airborne administration of an antigen. Blyth, D. I. et al., *Am. J. Respir. Cell Mol. Biol.*, 14(5):425–438, 1996. For example, animals can be sensitized to OVA, then challenged with methacholine. Sensitized mice develop leukocytic infiltrates of the airway lumen when treated with aerosolized allergen. The leukocytic infiltrates are dominated by CD4 lymphocytes and eosinophils. Sensitized mice also develop AHR and goblet cell hyperplasia with excessive mucus production.

Animals homozygous for inactivated MBP alleles fail to exhibit AHR upon OVA challenge. These animals perform similarly to homozygous animals challenged with saline as a control. In fact, AHR in response to methacholine challenge is proportional to the amount of MBP present, as heterozygous animals have an intermediate response. This observation is important because of its potential implication for human patients. Thus, asthma patients display AHR to airborne environmental assaults because their circulating levels of MBP are higher than "normal" patients. MBP deficient animals can be used in conjunction with established animal models of inflammation (e.g., OVA sensitization/aerosol-challenge in mice) to assess the effector function(s) of MBP and to screen for anti-MBP therapies. For example, MBP deficient mice can serve as controls with OVA sensitized/aerosol-challenged mice. Alternatively, a human MBP gene can be introduced into MBP knockout mice through knock-in or transgenic technology to provide an additional animal model of respiratory inflammation. In these mice, MBP is produced only from the human MBP gene. Thus, these mice have reduced endogenous MBP and have detectable levels of human MBP. As used herein, "detectable" refers to the ability to measure human MBP in the animal using standard techniques, including immunoassays and immunohistology.

Non-human mammals such as these mice can be used to screen for inhibitors of MBP effector function, using AHR as the endpoint. For example, AHR can be assessed in a first group of such non-human mammals in the presence of a compound, and compared with AHR in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. If AHR is reduced in the first group, the compound is identified as an inhibitor of MBP effector function. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

The invention will be further described in the following examples, which do not limit the scope of the invention as described in the claims.

EXAMPLES

Example 1

Purification of MBP

Figure 1:
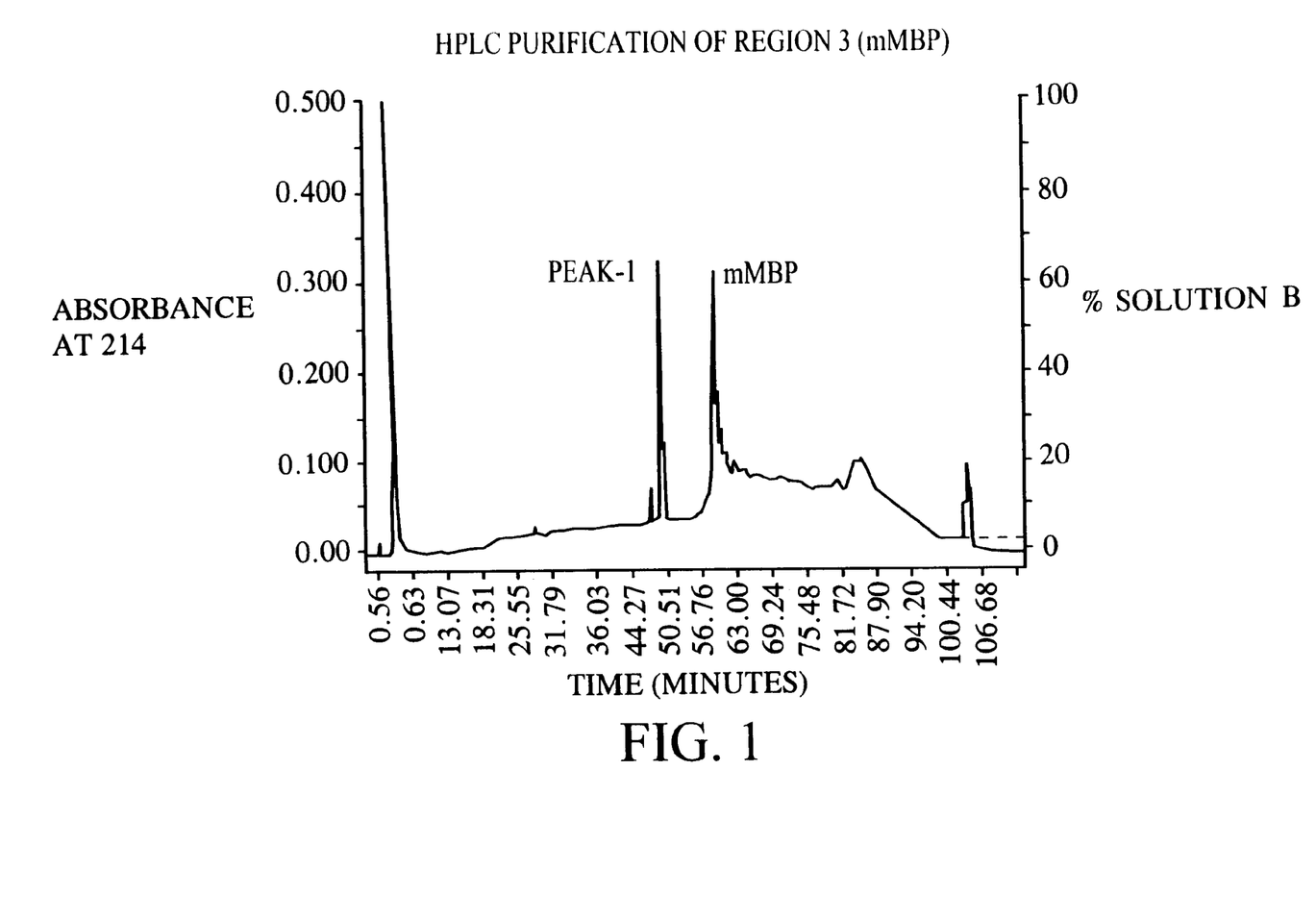
FIG. 1 is a chromatogram depicting purified mMBP.

Eosinophils can be purified using a Percoll step gradient. Secondary granules are released from purified eosinophils (p<1.080 g/ml) after osmotic lysis in 0.25M sucrose and high-speed centrifugation of the lysate. MBP is recovered from the granules by acid lysis and acid-soluble proteins are size fractionated using Sephadex G-50. The major secondary granule proteins fractionate into three distinct molecular weight groups designated as Region-1, -2 and -3. Sephadex G-50 fractions representing Region 3 were pooled and an aliquot of this material was visualized by SDS-PAGE. These data suggested that Region 3 represented a unique protein. Reverse-phase HPLC purification, however, showed that this "single polypeptide" was actually composed of two proteins, one of which subsequently has been identified as mMBP (FIG. 1).

Example 2

Immunofluorescence With a Polyclonal Antisera to Mouse Major Basic Protein

Purified mMBP was used to develop a polyclonal antisera to identify infiltrating tissue eosinophils and to act as a marker for the deposition of mMBP (i.e., eosinophil activation/degranulation) during inflammatory reactions. This reagent has been shown to be eosinophil specific and capable of detecting even low levels of mMBP released into the bronchial alveolar lavage (BAL) fluid of OVA sensitized/aerosolized-challenged mice. Lee, J. J. et al., *J. Exp. Med.*, 1997, 185:2143–2156.

Example 3 mMBP-Deficient Mice

Figure 2:
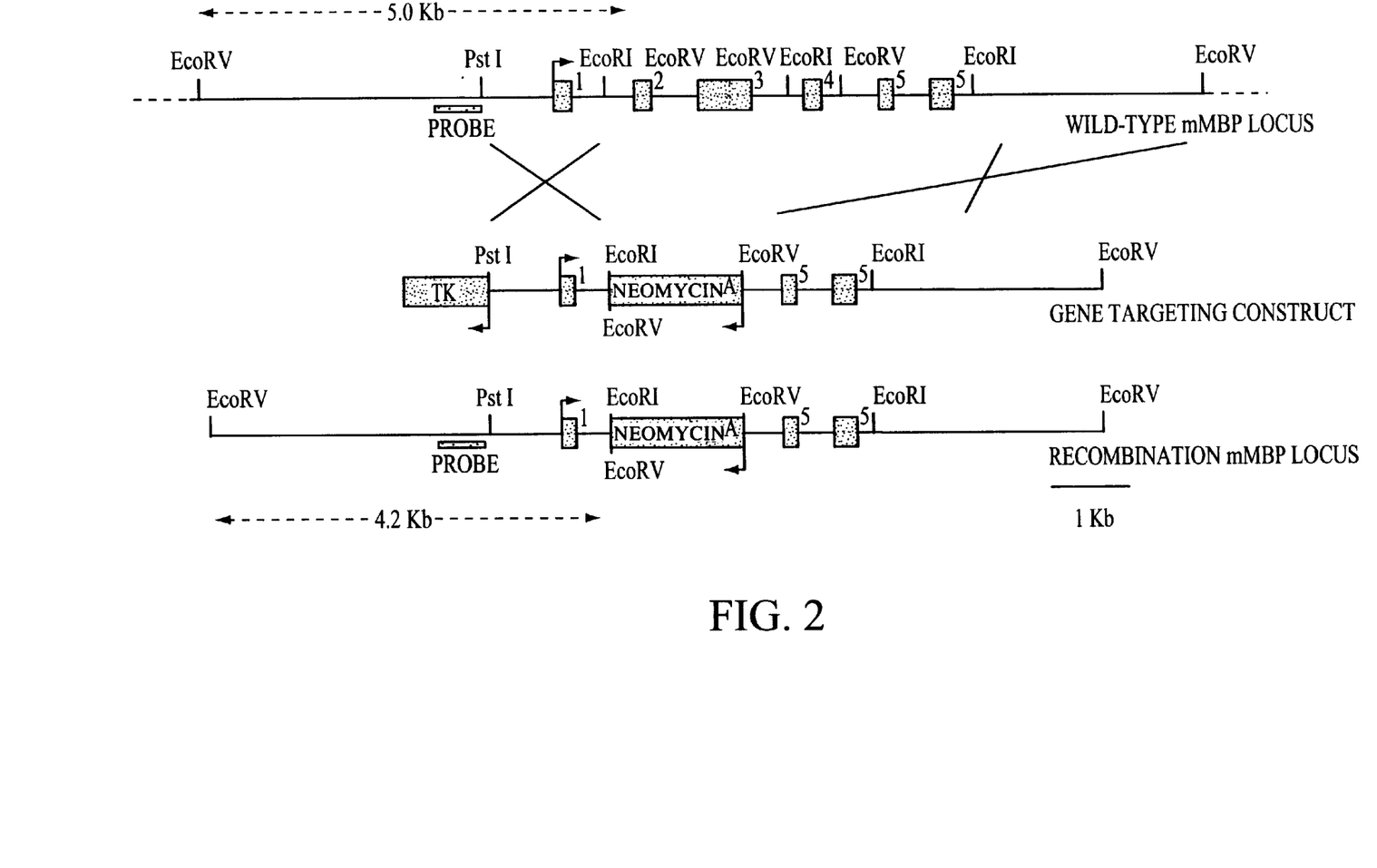
FIG. 2 is a diagram of the targeting construct of the mMBP gene. A partial restriction map (~12 kb) of wild-type genomic DNA, including the 6 exons of the mMBP gene, is shown on top. The probe indicated hybridizes to a 5.0 kb genomic fragment generated by EcoRV digestion. The targeting construct utilizes homology regions derived from mMBP flanking a Neo® gene and includes the herpes simplex thymidine kinase (TK) gene as a negative drug selection marker (middle). The resulting targeted locus after a correct homologous recombination event is shown at the bottom of the figure. The targeted allele generates a 4.2 kb fragment, when hybridized with the indicated probe, after digestion with EcoRV.

The cDNAs and genomic clones representing the mouse orthologue of the human MBP gene have been isolated and characterized. Larson, K. A. et al., *J. Immunol.*, 1995, 155(6):3002–3012. Murine MBP genomic clones from 129/SvJ-derived DNA were isolated to facilitate homologous recombination into syngeneic 129/SvJ ES cells. Restriction maps representing the mMBP locus and the gene targeting construct are shown in FIG. 2. This construct utilizes a positive (Neo® induced resistance to G418) and negative (viral TK activity in the presence of gancyclovir) double drug selection strategy. Homologous recombination induced a deletion of mMBP exons 2–4 (~3 kb), including the translational start site, the "pro" segment of the precursor polypeptide, and the N-terminal third of the mature MBP molecule stored in the secondary granule. The extensive nature of this deletion results in a complete loss of mMBP (i.e., a null allele). The predicted genomic structure of a targeted mMBP locus, together with restriction fragments used to characterize this locus, are also shown in FIG. 2.

Greater than 200 ES cell clones resulted from drug selection after transfection (via electroporation) of the targeting construct. Analyses of the ES cell clones via PCR and genomic Southern blot demonstrated a targeting frequency of the mMBP locus of ~5% (i.e., targeted clones relative to ES cell colonies surviving drug selection). DNA from isolated ES cell clones was digested with EcoRV. Hybridization was with the probe indicated in FIG. 2. Southern analysis indicated that there were three clones targeting one of the two mMBP alleles (clones 17, 52, 62). Other ES cell clones were wild-type (clones 20, 26, 27). The targeted allele and wild-type allele correspond to 4.2 kb and 5.0 kb fragments, respectively.

Southern blots also were performed with ES cell-derived genomic DNA that had been digested with Bgl II/Bsm I, using a Neo® derived fragment as a probe. The appearance of only a single fragment of the predicted size fragment (2.7 kb) indicated that these cells had only one copy of the Neo® gene and that the homologous recombination events were unique and not accompanied by additional random integration events of the targeting construct (i.e., other than the targeting event, no addition integration events involving this construct occurred in these ES cell clones).

Chromosome analysis of two independent (and randomly selected) ES cell clones carrying mMBP targeted alleles showed the normal modal number of 40 chromosomes and were subsequently used to produce chimeric animals by injection of the cells into C57BL/6J blastocytes. Each ES cell clone produced high percentage chimeras (i.e., >90%). Mice carrying a null allele for the mMBP gene were bred to homozygosity.

Example 4

Characterization of mMBP Null Mice

Figure 3A:
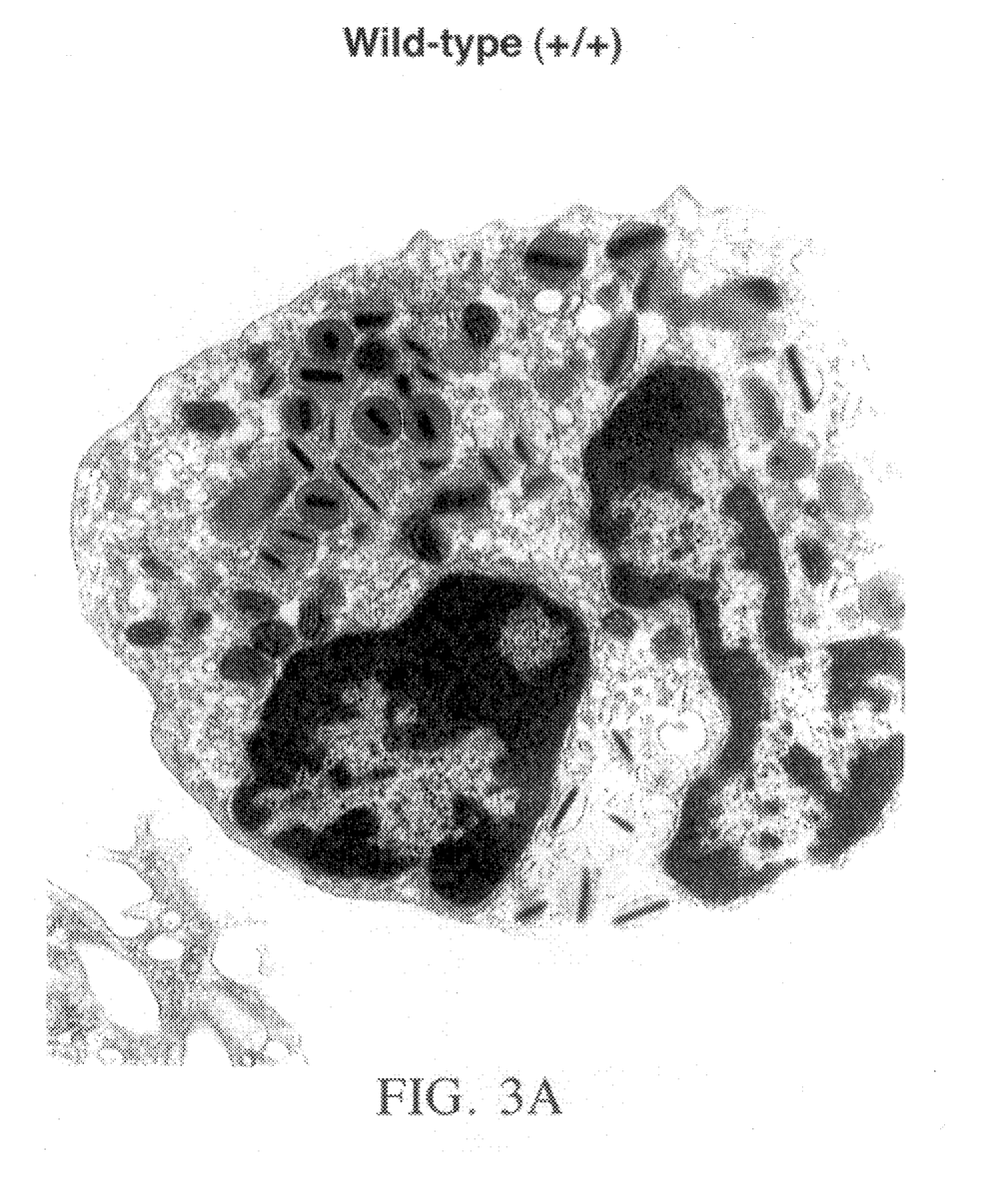
FIGS. 3A and 3B are electronmicrographs of eosinophils from MBP wild-type mice (3A) or MBP null mice (3B).
Figure 3B:
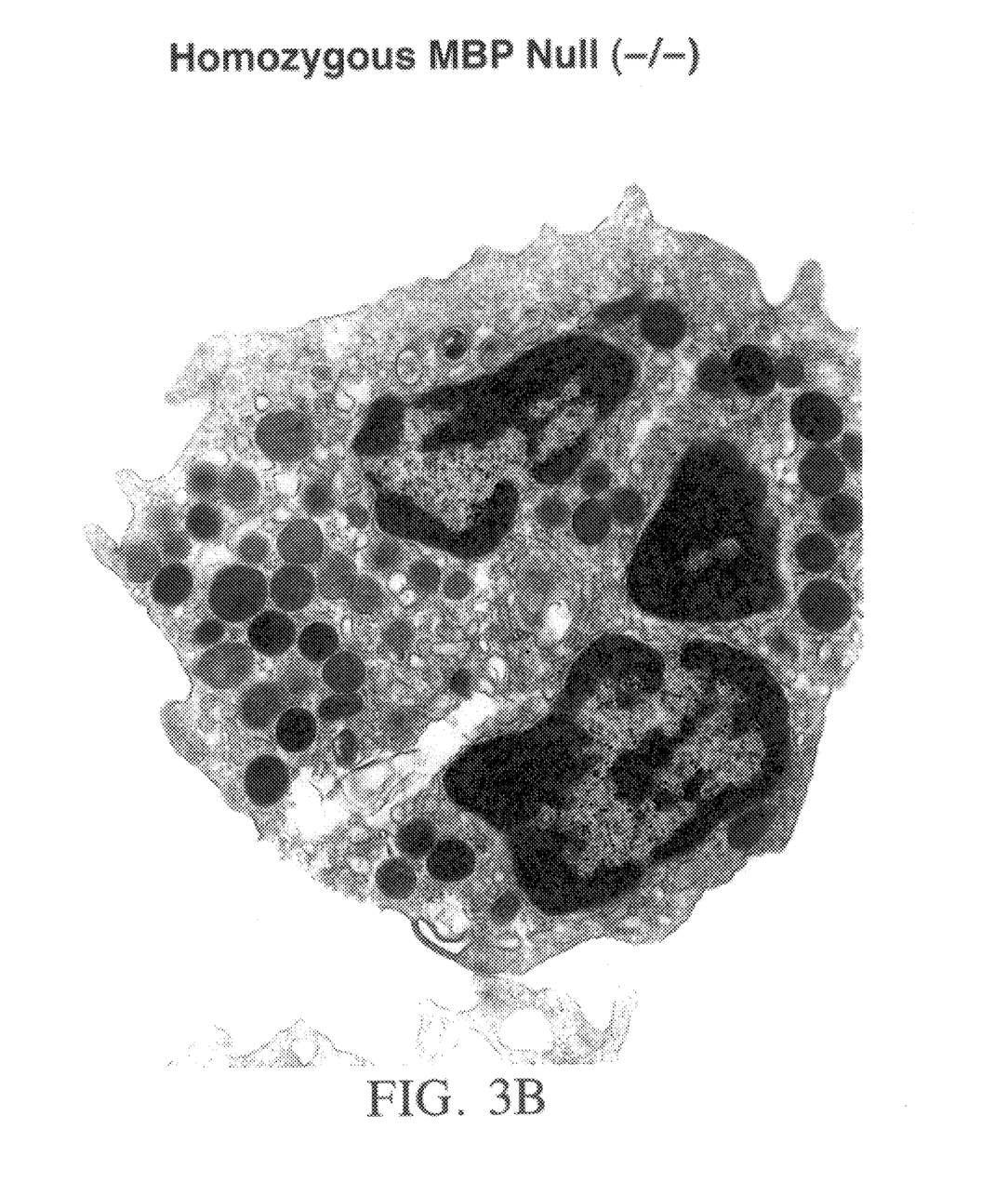

Electron microscopy was performed on peritoneal cavity derived eosinophils from wild-type (+/+) mice (FIG. 3A), heterozygous mMBP knock-out (−/+) mice, and homozygous mMBP (−/−) null animals (FIG. 3B) to determine if the formation of the electron dense core of mouse eosinophil secondary granules was dependent on the presence of mMBP. The results were striking in that homozygous null mice completely lost all evidence of the electron dense cores, suggesting that core formation is dependent (although not necessarily sufficient) on the presence of mMBP. It is of interest to note that mice heterozygous for the mMBP null allele generate eosinophil secondary granules with electron dense cores indistinguishable from wild-type.

Figure 4:
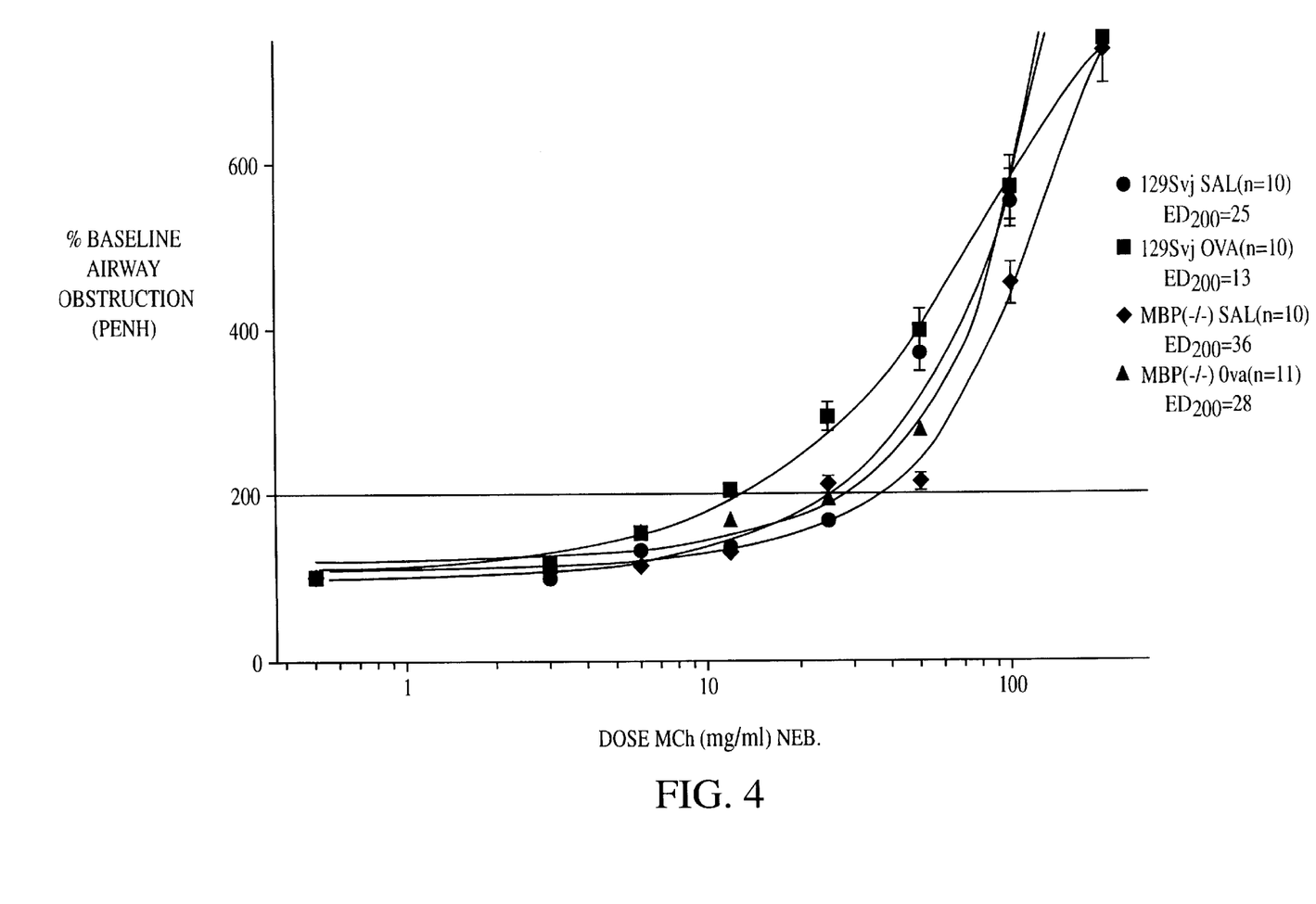
FIG. 4 is a graph that depicts percent baseline airway obstruction of wild-type R9 SVJ mice challenged with saline (●) or ovalbumin (■) and null mice challenged with saline (♦) or ovalbumin (▲).

AHR was measured in the null mice and control animals using whole-body plethysmography. See, Hamelmann, E. et al., *Am. J. Respir. Crit. Care Med.*, 156(3 Pt. 1):766–775, 1997. AHR was reported as a unit-less parameter called PENH (enhanced pause). AHR has been shown to correlate with airway resistance, relative to an increasing aerosol delivered dose of methacholine. Data derived from wild-type (129/SvJ) mice and homozygous mMBP knock-out mice (−/−) are shown in FIG. 4. The graph of FIG. 4 compares the responses of these mice (number of animals (n) per experimental group is shown next to each plot) to both a saline (Sal) aerosol challenge (control) as well as an ovalbumin (OVA) aerosol challenge (experimental). Sensitization and aerosol challenge of mice with OVA results in a type I hypersensitivity reaction (i.e., an allergic response) in the lungs of these mice. A comparison of the $ED_{200}$ values (i.e., the point at which the plots cross the 200% threshold) unambiguously show that only wild-type (129/SvJ) mice display AHR in response to a methacholine challenge. In contrast, the OVA induced response in mMBP knock-out mice is lost (compare the MBP(−/−) OVA plot (▲) with the MBP (−/−) Sal plot (♦). AHR in ovalbumin models of respiratory inflammation appears contingent upon the presence of mMBP. That is, this hallmark feature of asthma appears to result from the release of mMBP by eosinophils recruited to the lung in response to allergic inflammation.

Figure 5:
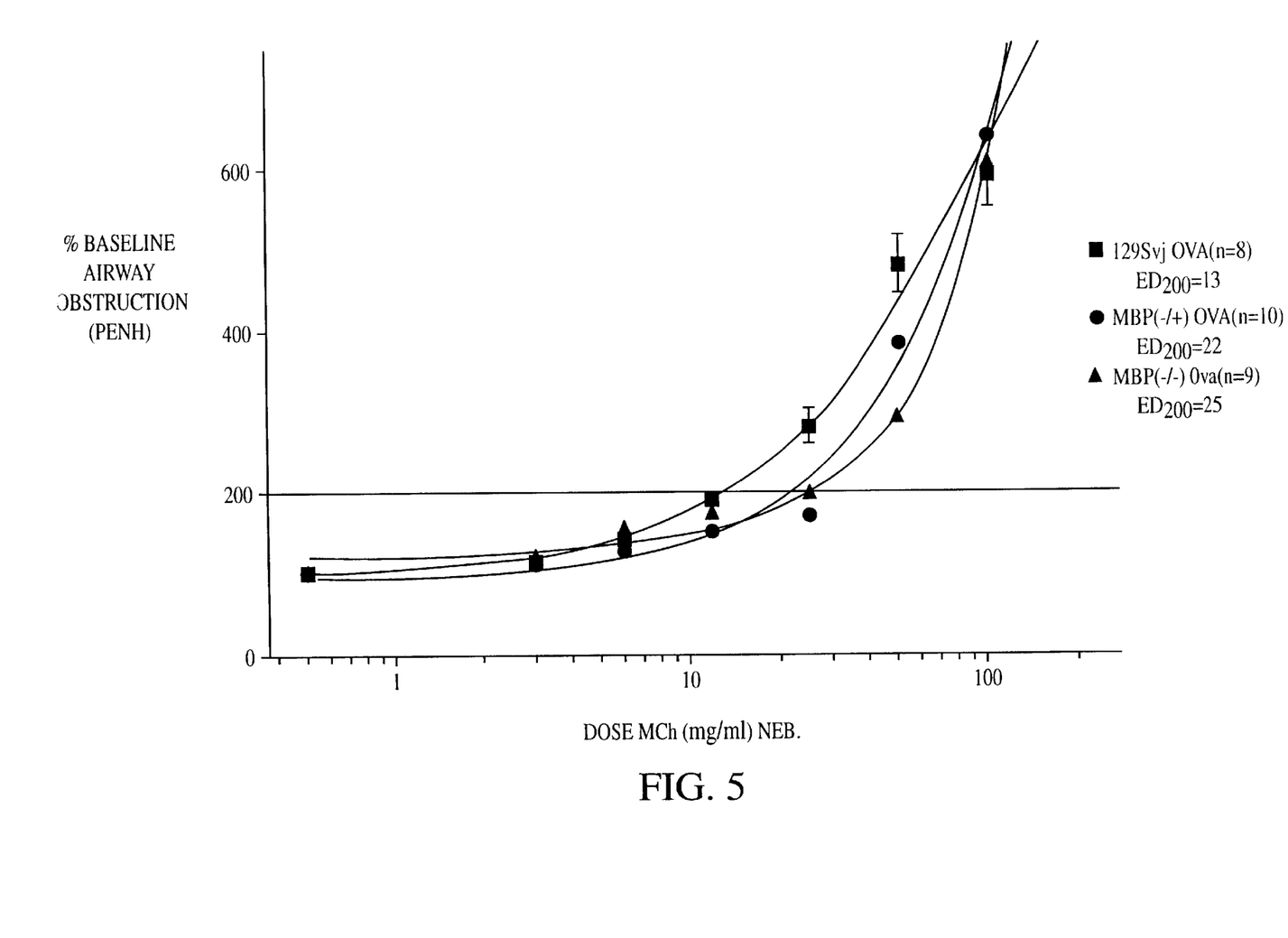
FIG. 5 is a graph that depicts the percent baseline airway obstruction in 129/SVJ MBP wild-type mice (■), 129/SVJ MBP heterozygous mice (●), and 129/SVJ homozygous mice (▲).

OVA-induced AHR among the three genotypes of mice, i.e., wild-type (129/SvJ), heterozygous mMBP knock-out (−/+), and homozygous mMBP null (−/−) animals, was assessed to determine if there was a MBP "dose" response to methacholine. In other words, it was determined if the inhibition of OVA-induced AHR was proportional to the amount of MBP present. It is assumed that heterozygous mice have approximately half the level of MBP of 129/SvJ mice. FIG. 5 shows the data derived from OVA challenge of 129/SvJ mice, heterozygous mice, and null mice. As before, the number of animals (n) per experimental group is shown next to each plot. These data clearly show that AHR in response to a methacholine challenge was proportional to the relative amount of available mMBP. This statement is derived from a comparison of the $ED_{200}$ values of the 129/SvJ OVA plot (■) relative to heterozygous mice (●), and null mice (▲). Again, it appears that AHR in ovalbumin models of respiratory inflammation is not only contingent upon the presence of mMBP, but that the degree of AHR is contingent upon the amount of mMBP present.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A DNA construct comprising a gene for the mouse major basic protein, wherein said gene for said mouse major basic protein is lacking exons 2, 3 or 4.

2. The DNA construct of claim 1, wherein said gene for said mouse major basic protein is lacking exons 2, 3 and 4.

3. A transgenic mouse whose genome comprises an engineered disruption of the endogenous mouse major basic protein gene, wherein said disruption causes decreased airway hyperresponsiveness upon sensitization with ovalbumin and aerosol challenge with ovalbumin followed by methacholine challenge as compared to wild-type mice.

4. The transgenic mouse of claim 3, wherein said transgenic mouse is heterozygous for said engineered disruption of the mouse major basic protein gene.

5. The transgenic mouse of claim 3, wherein said transgenic mouse is homozygous for said engineered disruption of the mouse major basic protein gene.

6. An eosinophil isolated from a transgenic mouse whose genome comprises an engineered disruption of the endogenous mouse major basic protein gene, wherein said disruption causes decreased airway hyperresponsiveness upon sensitization with ovalbumin and aerosol challenge with ovalbumin followed by methacholine challenge as compared to wild-type mice.

7. The eosinophil of claim 6, wherein said transgenic mouse is homozygous for said engineered disruption of the endogenous mouse major basic protein gene.

* * * * *

UNITED STATES PATENT AND TRADEMARK OFFICE
CERTIFICATE OF CORRECTION

PATENT NO. : 6,177,610 B1
DATED : January 23, 2001
INVENTOR(S) : James J. Lee and Nancy A. Lee It is certified that error appears in the above-identified patent and that said Letters Patent is hereby corrected as shown below:

<u>Title page,</u>
(75) Inventors: Please delete inventors "Karen L. Denzler" and "Steven C. Farmer"

Signed and Sealed this

Seventeenth Day of July, 2001

*Attest:*

NICHOLAS P. GODICI
*Attesting Officer*  *Acting Director of the United States Patent and Trademark Office*